United States Patent [19]

Kende et al.

[11] 4,164,503

[45] Aug. 14, 1979

[54] QUINONOID INTERMEDIATES FROM CHLOROPRENE

[75] Inventors: Andrew S. Kende, Pittsford, N.Y.; Yuh-Geng Tsay, San Jose, Calif.; Takuya Furuta, Rochester, N.Y.

[73] Assignee: Research Corporation, New York, N.Y.

[21] Appl. No.: 949,511

[22] Filed: Oct. 10, 1978

[51] Int. Cl.$^2$ .................... C07C 49/72; C07C 49/74; C07C 49/80; C09B 3/82
[52] U.S. Cl. ................................. 260/365; 260/383; 260/384
[58] Field of Search .............. 260/365, 396, 369, 383, 260/351, 559 AT

[56] References Cited

U.S. PATENT DOCUMENTS

| | | | |
|---|---|---|---|
| 3,803,124 | 4/1974 | Arcamone et al. | 260/365 |
| 4,021,457 | 5/1977 | Kende et al. | 260/383 |
| 4,070,382 | 1/1978 | Kende et al. | 260/365 |

OTHER PUBLICATIONS

*Chemical Abstract*, vol. 82, #169826c, "Polycyclic Quinone Charge Transfer Complexes", Medne et al., 1975.
*Chemical Abstract*, vol. 63, #16273b, "Rhodomycins IX Antibiotics from Actinomycetes", Brockmann et al., 1965.

*Primary Examiner*—Allen B. Curtis
*Assistant Examiner*—Raymond Covington
*Attorney, Agent, or Firm*—Omri M. Behr

[57] ABSTRACT

There is provided a novel and efficent method of synthesizing 7,10-dihydro-6,11-dihydroxy-5,9,12(8H)-naphthacenetrione and analogs thereof substituted in the 1,2,3 or 4 positions. The novel method comprises reacting the appropriate quinizarinquinone with a haloprene under Diels-Alder conditions, followed by aromatization and treatment with strong acid under very mild temperature conditions. The products of this process are important intermediates in the synthesis of daunomycin and its analogs which are useful in the therapy of neoplastic ailments.

28 Claims, No Drawings

QUINONOID INTERMEDIATES FROM CHLOROPRENE

The invention described herein was made in the course of work under a grant or award from the Department of Health Education and Welfare.

BACKGROUND OF THE INVENTION

Adriamycin, an antibiotic compound which is useful in the treatment of certain tumors is described and claimed in U.S. Pat. No. 3,590,028 to Arcamone et al. A further procedure for the preparation of adriamycin will be found in U.S. Pat. No. 3,803,124 to Arcamone et al which also discloses that adriamycin may be prepared from daunomycin or its aglycone daunomycinone. The coupling of daunomycinone with the appropriate sugar to yield daunomycin (also known as daunorubicin) is found in Acton, et al J.Med.Chem. 17, 659 (1974).

Certain analogs of daunomycin which are disclosed as being useful in the therapy of neoplastic ailments are set forth in Belgian Pat. No. 830,090 to Patelli, et al Societa Farmaceutici Italia, S.p.a. Included among these analogs are 4-demethoxydaunomycin,1-methoxydaunomycin,1,4-and 2,3-dimethyl-4-demethoxydaunomycin.

Methods of synthesizing daunomycinone are disclosed in Kende, et al U.S. Pat. No. 4,070,382 and the analogs thereof in Kende, et al U.S. Pat. No. 4,021,457 which are both incorporated herein by reference.

In both of the above-identified Kende, et al methods the key step in providing the tetracyclic skeleton involves a Diels-Alder reaction between the appropriate quinizarinquinone (I) and an ester of 2-hydroxy-1,3-butadiene most suitably the acetyl ester.

It has been found that the necessary esters of 2-hydroxy-1,3-butadiene are difficult and expensive to prepare and efforts were directed to the provision of an inexpensive, readily available alternative diene which would provide not only the desired tetracyclic skeleton but also a moiety at the 9 position of said skeleton which could be readily converted to the desired 9-keto group.

SUMMARY OF THE INVENTION

It has been found that when quinizarinquinone (I) or the analogs thereof substituted in the 5 through 8 positions is reacted with a haloprene there is produced, in good yield, the corresponding 9-halo 6a,7,10,10a-tetrahydro-5,6,11,12-naphthacenetetraone (II).

A reaction of this tetraone with a proton acceptor or proton donor in a suitable solvent yields the corresponding 9-halo 7,10-dihydro-6,11-dihydroxy-5,12-naphthacenedione (III).

Where any of the substituents at $C_1$–$C_4$ is other than hydrogen, then the Diels-Alder reaction is run above room temperature and contains a mixture of (II) and (III).

It is our surprising finding that normal acid hydrolysis conditions ie, sulfuric acid in refluxing acetic acid will destroy the product (III). It is our further surprising finding that if the hydrolysis is carried out under extremely mild conditions, for example commencement of the reaction at ice bath temperatures with slow warming to ambient temperatures, the hydrolysis proceeds in excellent yield to give the desired 7,10-dihydro-6,11-dihydroxy-5,9,12(8H)naphthacenetrione (IV).

The general reaction scheme is set forth herein below.

$R_2$ and $R_3$ are hydrogen or alkyl $R_1$ and $R_4$ are hydrogen, hydroxy, alkyl, phenyl-or substituted phenyl-alkyl, alkoxy, phenyl-or substituted phenyl-alkoxy wherein the substituents $R_1$ and $R_4$ may be the same as or different from the substituents $R_2$ and $R_3$. X is halo.

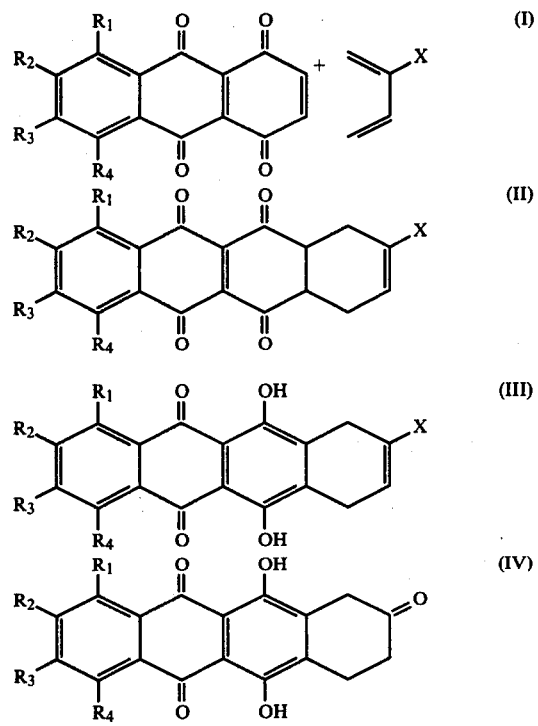

DESCRIPTION OF THE PREFERRED EMBODIMENTS

The starting materials of the process of the present invention may be considered to be the compounds of formula I. The quinizarinquinones of this general formula may be prepared by methods set forth in either of the two Kende, et al U.S. Pat. Nos. 4,021,457 or 4,070,382.

In this starting material $R_2$ or $R_3$ may be hydrogen, or alkyl, suitably lower-alkyl of 1 to 5 carbon atoms, most suitably methyl. $R_1$ or $R_4$ may be hydrogen hydroxy, alkyl, suitably lower-alkyl, phenyl-or substituted phenyl-lower alkyl wherein the substituent groups are lower alkyl, lower alkoxy, or halo wherein the term lower alk signifies a straight or branched chain hydrocarbon moiety containing 1 to 5 carbon atoms. $R_1$ or $R_4$ may also be alkoxy suitably lower alkoxy, phenyl-or substituted phenyl-lower alkoxy wherein the substituent groups are lower alkyl, lower alkoxy or halo wherein, similarly, lower alk signifies a straight or branched chain hydrocarbon moiety having 1 to 5 carbon atoms.

While the invention is in no way limited thereto, preferred compounds within the scope of the present invention are those wherein $R_2=R_3=$hydrogen, $R_1$ is hydrogen and $R_4$ is hydrogen, hydroxy or alkoxy, most suitably methoxy or $R_2=R_3$ and $R_1=R_4$ wherein $R_1=$alkoxy and $R_2=$alkyl.

It should be noted that where $R_2=R_3$ and $R_1=R_4$ the reaction sequence will yield a single regiospecific product. The regiospecific product will also be obtained when the $R_1$, $R_2$, $R_3$ and $R_4$ are all the same. On the other hand where asymmetric substitution is present in the aromatic ring of the quinizarinquinone (for example $R_2$=hydrogen $R_1$=hydrogen and $R_4$=methoxy) a regioisomeric mixture is produced.

In order to be consistent with the nomenclature usually utilized in this field of the art the substitutent in the far right hand ring (A-ring) of the tetracyclic moiety is always designated as the 9-substitutent. Thus there would in the immediately foregoing example, be provided a regioisomeric mixture of 9-halo7,10-dihydro-1-or 4-methoxy-5,6,11,12-naphthacenetetraone (II). Such a regioisomeric mixture (II) is then treated in the same manner as the regiopecific material and the resolution of the ultimate product into the respective regioisomers is carried out in a manner well-known to those skilled in the art particularly as set forth in the two Kende patents referred to herein.

In the preferred procedure the quinizarinquinone (1) and a solution of haloprene in a reaction inert organic solvent are mixed and heated, preferably in the presence of an organic acid. The reaction may be carried out in polar or non-polar solvents, hydrocarbon solvents such as aromatic hydrocarbon solvents, for example xylene or toluene may be employed, similarly halogenated hydrocarbons such as chloroform or methylene chloride may be used, equally mixtures of both of these groups of solvents may be employed. To improve the yield of the desired product it has been found advantageous to employ an organic acid as solvent or cosolvent. It has been found that lower alkanoic acids, suitably acetic acid are preferred. It has been found suitable to prepare a solution of between 5 and 15% by weight of the reactants in a solvent mixture of the inert solvent and the acid. The use of glacial acetic acid as a solvent has been found especially suitable. There is employed an excess of the haloprene over the quinizarinquinone. A ratio of 3 moles of haloprene to each mole of quinizarinquinone is especially preferred.

The reaction conditions employed in the Diels-Alder reactions vary in accordance with the substitution pattern in the aromatic ring. Thus the reaction may be run at between about 20° C. and about 100° C. for about 1 to about 3 days. It has been found especially suitable to run the reaction at about 70° C. for about 24 hours with stirring, where the aromatic ring is substituted.

After cooling the reaction mixture to ambient temperature it is diluted with a water immiscible solvent, suitably with diethylether and the thus formed precipitate (adduct II) is precipitated and removed by filtration. The precipitate is washed suitably with ether and dried under reduced pressure in the presence of a drying agent suitably phosphorus pentoxide.

Where the substituent at $C_1$ to $C_4$ is other than hydrogen, it is desirable to run the reaction at the higher end of the temperature scale set forth above. Under these conditions there is formed not only the adduct (II) but also a certain amount of the corresponding enol (III).

It is not necessary to purify the adduct (II) further whether or not it contains any of the enolized product III, since it is then enolized to the phenolic tautomer. The enolization is achieved by treatment of (II) with a proton acceptor or proton donor in a suitable organic solvent. It has been found that salts of alkanoic, aroic or aralkanoic acid, such as acetates, butyrates, benzoates, naphthoates, phenyl acetates, phenyl propionates, and the like in the presence of the corresponding acid, suitably the same acid as that forming the anion of the salt, may be employed. The preferred conditions include, for example, warming the compound in an alkanoic acid solvent containing either an alkali salt of that acid, or mineral acid, or p-toluene sulfonic acid. In the preferred variant of the reaction, the adduct is dissolved in glacial acetic acid at a temperature just below its boiling point, and the proton acceptor, preferably anhydrous sodium acetate, added thereto. There need only be utilized between 0.1 and 0.3 moles of the proton acceptor per mole of adduct, although an excess is generally used. The enolization takes place very rapidly, but it is desirable to continue heating for 1 or 2 minutes after the addition. The reaction mixture is then cooled to ambient temperature, sufficient water added to precipitate the enolized adduct which is then separated suitably by filtration, washed, and dried under reduced pressure to yield the dihydroxynaphthacenedione (III).

If desired dione (III) may be further purified by recrystalization, suitably from glacial acetic acid.

The halodione (III) is then hydrolyzed to the corresponding 9-ketone (IV). While it is preferred to carry out this hydrolysis using strong acid the temperature of the reaction should be reduced as far as possible. It has been found that a temperature range of $-5°$ C. through 25° C. is suitable. In the most preferred modification there is prepared a mixture of a strong mineral acid and an alkanoic acid suitably a lower alkanoic acid such as formic acid, acetic acid, or propanoic acid, glacial acetic acid being especially preferred. The strong acid should preferably by anhydrous. Among the preferred acids are strong mineral acids most suitably concentrated sulfuric acid or phosphoric acid. The acids are mixed in a ratio of from about 1 to about 10 parts of strong acid to 1 part by volume of alkanoic acid. A substantial excess that is to say at least (although not critically so) a 3- molar excess of strong acid to halodione (III) is preferred.

In the most preferred procedure the acid mixture is cooled in a cooling bath suitably in ice water bath to about 0° C. and the halodione (III) added thereto with stirring. After addition is complete the external cooling is gradually removed and the mixture permitted to warm to ambient temperature over a period from about 2 to about 5 hours at which temperature stirring is continued for about 24 hours.

The reaction is then quenched suitably by pouring onto ice and the product extracted therefrom with a reaction inert water immiscible organic solvent suitably a polar solvent such as methylene chloride or chloroform, chloroform being preferred. The aqueous acid mixture is extracted several times and the combined extracts washed, suitably with sodium bicarbonate and water, dried and the solvent under reduced pressure to yield the so-called "red ketone" (IV). Further purification of this ketone is not necessary. As stated hereinabove this ketone may be a regiospecific compound or it may be a regioisomeric mixture depending upon the starting material utilized.

The red ketone is then converted into the desired end product by methods well-known in the art.

EXAMPLES

EXAMPLE I

9-Chloro-6a,7,10,10a-tetrahydro-5,6,11,12-naphthacenetetraone (II)

Quinizarinquinone (I) (1.0 g, 4.2 mmol) and chloroprene (1.12 g, 12.6 mmol) were dissolved in acetic acid (6 ml, glacial) and stirred at ambient temperature under nitrogen for 2.5 days. The reaction mixture was then diluted with ether (25 ml), the reaction mixture filtered, the retained precipitate washed with ether and dried under reduced pressure in the presence of phosphorus pentoxide to yield 9-chloro-6a,7,10,10atetrahydro-5,6,11,12-naphthacenetetraone (II) (988 mg, 72%). Recrystalization (chloroform-ether) gave the foregoing compound in analytical purity m.p. 221°–222° C., ir (KBr): 5.85, 6.02, 630μ; uv (CHCl$_3$): 353, 266, 259, 241 nm; ms (70 eV): 328 (M+ +2, 50), 326 (M+, 44), 324 (M+ −2, 50), 291 (47), 275 (25), 240 (100); Anal. Calcd. for C$_{18}$H$_{11}$ClO$_4$: C, 66.16; H, 3.39; Found: C, 66.33; H, 3.36.

EXAMPLE II

Regioisomeric Mixture of 1-methoxy and 4-methoxy-9-chloro 6a,7,10,10a-tetrahydro-5,6,11,12-naphthacenetetraone (II)

A mixture of 5-methoxy-1,4,9,10-anthradiquinone (456 mg, 1.70 mmol) (I) and chloroprene (452 mg, 5.10 mmol) in acetic acid (5 ml, glacial) were heated under nitrogen for 24 hours at 70° C. with stirring. The reaction mixture was cooled to ambient temperature, diluted with ether (25 ml) and the reaction mixture filtered. The residue was washed with ether and dried under reduced pressure in the presence of phosphoruspentoxide to yield a regioisomeric mixture of 1-methoxy and 4-methoxy-9-chloro-6a,7,10,10a-tetrahydro-5,6,11,12-naphthacenetetraone (II) together with the regioisomeric mixture of 1-methoxy- and 4-methoxy-9-chloro-7,10dihydro-6,11-dihydroxy-5,12-naphthacenedione (III) as a minor component (370 mg) which was not further purified.

In accordance with the above procedure but where, in place of 5methoxy-1,4,9,10-anthradiquinone there is utilized 5-hydroxy-,5-benzoxy- or 5-methyl-1,4,9,10-anthradiquinone there is obtained the corresponding regioisomeric mixture of 1-hydroxy- and 4-hydroxy-,1-benzoxy-and 4-benzoxy-, or 1-methyl-and 4-methyl-9-chloro-6a,7,10,10a-tetrahydro-5,6,11,12-naphthacenetetraones together with some of the corresponding 6,11-dihydroxy-5,12-napthacenedione (III) as a minor component.

In accordance with the forgoing procedure but starting with 5,8-dihydroxy-,5,8-dimethyl-,6,7-dimethyl-,5,8-dimethoxy-,5,8-benzoxy-, or 5,8-dimethoxy-6,7-dimethyl-1,4,9,10-anthradiquinone there is obtained the corresponding 1,4-dihydroxy-,1,4-dimethyl-2,3-dimethyl-,1,4dimethoxy-,1,4-dibenzoxy- or 1,4-dimethoxy-2,3-dimethyl 6a,7,10,10a-tetrahydro-5,6,11,12-naphthacenetetraone respectively together with some of the corresponding 6,11-dihydroxy-5,12-naphthacenedione (III) as a minor component.

In accordance with the foregoing procedures but where in place of chloroprene there is utilized bromoprene there is obtained the corresponding 9-bromonaphthacene derivative.

EXAMPLE III

9-Chloro-7,10-dihydro-6,11-dihydroxy-5,12-naphthacenedione (III)

The tetraone (II) produced in Example I (234 mg 0.716 mmol) was taken up in glacial acetic acid (3 ml) to which was added sodium acetate (82 mg, 1.00 mmol). The mixture was heated at 115° C. for 20 minutes, allowed to cool to ambient temperature and diluted with ether (15 ml). A precipitate is given which is separated from the reaction mixture by filtration, the residue washed sequentially with water and ether and dried under reduced pressure in the presence of phosphorus pentoxide to yield the desired aromatized chlorodione III (211 mg, 90.2%).

Recrystalization yields 9-chloro-7,10-dihydro6,11-dihydroxy-5,12-naphthacenedione (III) (from acetic acid) m.p. 287.5°–289° C.

ir (KBr): 6.10, 6.27μ; uv (CHCl$_3$): 518, 504, 484, 464, 322, 286, 258, 256 nm; ms (70 eV): 328 (M+ +2, 24), 326 (M+, 78), 324 (M+ −2, 42), 308 (10), 292 (20), 291 (100), 290 (26).; Anal. Calcd. for C$_{18}$H$_{11}$ClO$_4$: C, 66.16; H, 3.39; Found: C, 66.18; H, 3.25.

EXAMPLE IV

Regioisomeric Mixture of 1-methoxy-and 4-methoxy-9-chloro-7,10-dihydro-6,11-dihydroxy-5,12-naphthacenedione (III)

The crude tetraone produced in example II (370 mg) was taken up in glacial acetic acid (4.4 ml) to which is added sodium acetate (119 mg, 1.45 mmol). The mixture was heated at 110° C. for 25 minutes, allowed to cool to ambient temperature and diluted with water (15 ml). A precipitate was given which was separated from the reaction mixture by filtration, the residue washed sequentially with water and ether and dried under reduced pressure in the presence of phosphoruspentoxide to yield the desired aromatized chlorodione (III). Recrystallization yields the regioisomeric mixture of 1-methoxy-and 4-methoxy-9-chloro-7,10-dihydro-6,11-dihydroxy-5,12naphthacenedione (IV) (310 mg, 51%) (from acetic acid) m.p. 226°–269° C.

ir (KBr): 2.90, 6.19, 6.34μ; uv (CHCl$_3$): 533, 515, 496, 485, 474, 377, 285, 246, 244 nm; ms (70 eV: 358 (M+ +2, 33), 356 (100), 321 (60), 306 (29); Anal. Calcd. for C$_{19}$H$_{13}$ClO$_5$: C, 63.96; H, 3.67; Found: C, 63.75; H, 3.70.

In accordance with the above procedure but where, in place of 1-methoxy and 4-methoxy-9-chloro-6a,7,10,-10a-tetrahydro-5,6,11,12-naphthacenetetraone there are utilized any of the regioisomeric mixtures of naphthacenetetraones or regiospecific naphthacenetetraones produced in example III there are obtained the corresponding 9-halo-7,10-dihydro-6,11-dihydroxy-5,12-naphthacenediones respectively.

EXAMPLE V 7,10-Dihydro-6,11-dihydroxy-5,9,12(8H)-naphthacenetrione (IV)

There was prepared a mixture of glacial acetic acid (0.3 ml and concentrated sulfuric acid) 1.5 ml (which was cooled to 0° C. in an ice water bath). To this acid mixture was added 9-chloro-7,10-dihydro-6,11-dihydroxy-5,12-naphthacenedione (III) in a single batch and the mixture stirred. The mixture was permitted to warm slowly to ambient temperature over 3 hours at which temperature it was stirred for a further 24 hours. At the conclusion of this time the mixture was poured onto ice (ca. 25 g) and the organic layer extracted with chloroform (25 ml, ×4) the chloroform extracts were combined, washed with saturated aqueous sodium bicarbonate, and with water, dried over anhydrous sodium sulfate, filtered, and the solvent removed from the filtrate under reduced pressure. The residue was washed with ether and further dried in vacuo to yield the "red ketone" 7,10-dihydro-6,11dihydroxy-5,9,12(8H)naphthacenetrione (IV) (18 mg, 76%). This product was shown to be homogeneous by thin layer chromatographic analysis and had the same $R_f$ as an authentic sample (silica gel, 0.7% methanolic chloroform, $R_f=0.59$.

ir (KBr): 2.92, 5.82, 6.18, 6.34μ; uv (CHCl₃): 519, 506, 485, 464, 328, 282, 258, 253 nm; ms (70 eV): 308 (M+, 72), 280 (21), 266 (100).

In accordance with the above procedure but in place of utilizing acetic acid in the acid component there is utilized formic acid or propionic acid there is obtained the same product. Similarly, where concentrated phosphoric acid is utilized in place of concentrated sulfuric acid there is obtained the same product. Also where in place of the foregoing mixtures of organic and inorganic acids only the inorganic component is utilized there is obtained the same product.

In accordance with the above procedure but starting with 1,4-dihydroxy-,1,4-dimethyl-,2,3-dimethyl-,1,4-dimethoxy-, 1,4-dibenzoxy- or 1,4-dimethoxy-2,3-dimethyl-9-chloro-7,10-dihydro6,11-dihydroxy-5,12-naphthacenediones (III) there are obtained the corresponding 1,4-dihydroxy-,1,4-dimethyl-,2,3-dimethyl-,1,4-dimethoxy-,1,4-dibenzoxy or 1,4-dimethoxy-2,3-dimethyl-7,10-dihydro-6,11-dihydroxy-5,9,12(8H)-naphthacenetriones (IV).

EXAMPLE VI

Regioisomeric Mixture of 1-Methoxy and 4-Methoxy-7,10-dihydro-6,11-dihydroxy-5,9,12(8H)-naphthacenetrione (IV)

Concentrated sulfuric acid (0.5 ml) was cooled to 0° C. in an ice-water bath and there is added thereto, after cooling, the regioisomeric mixture of 1-methoxy- and 4-methoxy-9,chloro-7,10-dihydro-6,11-dihydroxy-5,12-naphthacenedione (III) (10 mg, 0.0280 mmol) produced in accordance with the example IV in one batch with stirring. The mixture was allowed to warm slowly to ambient temperature over 4 hours and stirring continued for a further 20 hours at this temperature.

The reaction mixture was then quenched by pouring onto ice (50 g) and the organic component extraxted with chloroform (25 ml,×4). The extracts were combined, washed with saturated aqueous sodium bicarbonate and water, dried over sodium sulfate, filtered, and the solvent removed from the filtrate under reduced pressure to give a red solid. Thin layer chromatography (silica gel, 1.5% methanolic chloroform) yielded 2 spots, a major spot, $R_f$ 0.60 and a minor spot $R_f$ 0.39. The major spot corresponds to the $R_f$ value of an authentic sample of regioisomeric mixture of 1-methoxy- and 4-methoxy-7,10-dihydro-6,11-dihydroxy-5,9,12(8H)-naphthacenetrione (IV) yield 59%.

ms (70 eV): 338 (M+, 100), 310 (29), 296 (48).

In accordance with the above procedure but starting with regioisomeric mixture of 1-hydroxy- and 4-hydroxy-,1-methyl- and 4-methyl-, or 1-benzoxy- and 4-benzoxy-9-chloro-7,10-dihydro-6,11-dihydroxy-5,12-naphthacenedione (III) there are obtained the corresponding regioisomeric mixtures of 1-hydroxy- and 4-hydroxy-,1-methyl- and 4-methyl-, or 1-benzoxy- and 4-benzoxy-7,10dihydro-6,11-dihydroxy-5,9,12(8H)-naphthacenetriones (IV) respectively.

We claim:

1. A compound of the formula

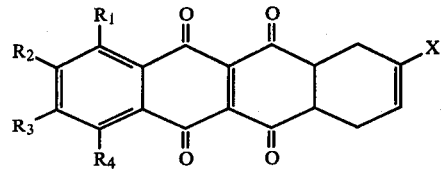

wherein:
X is halo,
R₁, R₂, R₃, and R₄ are the same or different, R₁ and R₄ are selected from the group consisting of hydrogen, hydroxy, lower alkyl, phenyl or substituted phenyl-lower alkyl wherein the substituent groups are lower alkyl lower alkoxy or halo, lower alkoxy, phenyl-or substituted phenyl-lower alkoxy wherein the substituent groups are lower alkyl lower alkoxy or halo, wherein lower alk signifies a branched chain or straight chain hydrocarbon moiety of 1 to 5 carbon atoms,
R₂ and R₃ are selected from the group consisting of the hydrogen, lower alkyl, phenyl-or substituted phenyl-lower alkyl wherein the substituent groups are lower alkyl, lower alkoxy or halo wherein lower alk signifies a branched or straight chain hydrocarbon moiety of 1 to 5 carbon atoms.

2. A compound of claim 1 wherein: R₁=R₂=R₃=R₄=hydrogen and X is chloro or bromo.

3. A regioisomeric mixture consisting substantially of two compounds of claim 1 wherein: R₁=R₄=H, R₂=R₃ or H and R₃=R₂ or H provided that in one of said compounds R₂=H and in the other R₃=H.

4. A regioisomeric mixture consisting substantially of two compounds of claim 1 wherein: R₂=R₃=H, and R₁=R₄ or H and R₄=R₁ or H provided that in one of said compounds R₁=H and in the other R₃=H.

5. A compound according to claim 1 wherein: R₁=R₄=H and R₂=R₃=other than H.

6. A compound according to claim 1 wherein: R₂=R₃=H and R₁=R₄ =other than H.

7. A compound of claim 3 wherein: R₂=methyl or hydrogen and R₃=hydrogen or methyl.

8. A compound of claim 4 wherein: R₁=methyl or hydrogen and R₄=hydrogen or methyl.

9. A compound of claim 4 wherein: R₁=methoxy or hydrogen and R₄ is hydrogen or methoxy.

10. A compound of claim 5 wherein: R₂=R₃=methyl.

11. A compound of claim 6 wherein: R₁=R₄=methyl.

12. A compound of claim 6 wherein: R₁=R₄=methoxy.

13. A compound of the formula

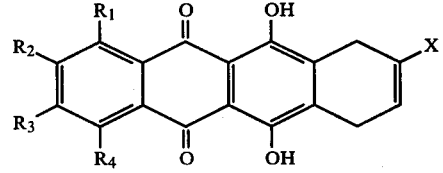

wherein:
X is halo,
R₁, R₂, R₃, and R₄ are the same or different, R₁ and R₄ are selected from the group consisting of hydrogen, hydroxy lower alkyl, phenyl or substituted phenyl-lower alkyl wherein the substituent groups are lower alkyl lower alkoxy or halo, lower alkoxy, phenyl-or substituted phenyl-lower alkoxy wherein the substituent groups are lower alkyl lower alkoxy or halo, wherein lower alk signifies a branched chain or straight chain hydrocarbon moiety of 1 to 5 carbon atoms, $R_2$ and $R_3$ are selected from the group consisting of the hydrogen, lower alkyl, phenyl-or substituted phenyl-lower alkyl wherein the substituent groups are lower alkyl, lower alkoxy or halo wherein lower alk signifies a branched or straight chain hydrocarbon moiety of 1 to 5 carbon atoms.

14. A compound of claim 1 wherein: $R_1=R_2=R_3=R_4=$hydrogen and X is chloro or bromo.

15. A regioisomeric mixture consisting substantially of two compounds of claim 1 wherein: $R_1=R_4=H$, $R_2=R_3$ or H and $R_3=R_2$ or H provided that in one of said compounds $R_2=H$ and in the other $R_3=H$.

16. A regioisomeric mixture consisting substantially of two compounds of claim 1 wherein: $R_2=R_3=H$, and $R_1=R_4$ or H and $R_4=R_1$ or H provided that in one of said compounds $R_1=H$ and in the other $R_3=H$.

17. A compound according to claim 1 wherein: $R_1=R_4=H$ and $R_2=R_3=$other than H.

18. A compound according to claim 1 wherein: $R_2=R_3=H$ and $R_1=R_4=$other than H.

19. A compound of claim 3 wherein: $R_2=$methyl or hydrogen and $R_3=$hydrogen or methyl.

20. A compound of claim 4 wherein: $R_1=$methyl or hydrogen and $R_4=$hydrogen or methyl.

21. A compound of claim 4 wherein: $R_1=$methoxy or hydrogen and $R_4$ is hydrogen or methoxy.

22. A compound of claim 5 wherein: $R_2=R_3=$methyl.

23. A compound of claim 6 wherein: $R_1=R_4=$methyl.

24. A compound of claim 6 wherein: $R_1=R_4=$methoxy.

25. A process for the preparation of a compound having the formula

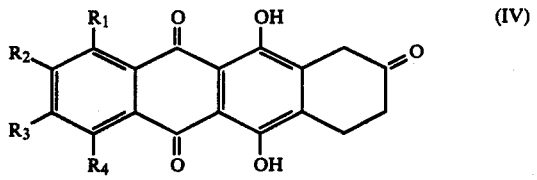

which comprises treating a compound having the formula

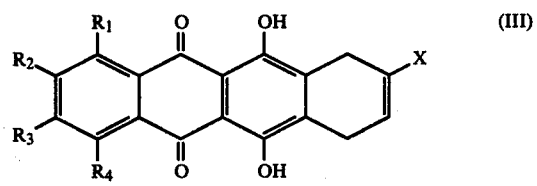

wherein:
$R_1$, $R_2$, $R_3$, $R_4$, and X are as in claim 1
with substantially anhydrous strong mineral acid at a temperature of between $-5°$ C. and + about 25° C.

26. A process in accordance with claim 25 wherein: the mineral acid is concentrated sulfuric acid or concentrated phosphoric acid.

27. A process in accordance with claim 26 wherein: the concentrated mineral acid is utilized in conjunction with a lower alkanoic acid of 1 to 5 carbon atoms.

28. A process in accordance with claim 27 wherein: the alkanoic acid is formic acid, acetic acid, or propionic acid.

* * * * *